United States Patent [19]
Renauld et al.

[11] Patent Number: 5,789,237
[45] Date of Patent: Aug. 4, 1998

[54] NUCLEIC ACID SEQUENCES CODING FOR OR COMPLEMENTARY TO NUCLEIC ACID SEQUENCES CODING FOR INTERLEUKIN 9 RECEPTOR

[75] Inventors: Jean-Christophe Renauld, Herbeunont; Catherine Druez, Sint-Stevens-Woluwe; Jacques Van Snick, Kraainem, all of Belgium

[73] Assignee: Ludwig Institute for Cancer Research, New York, N.Y.

[21] Appl. No.: 164,614

[22] Filed: Dec. 8, 1993

Related U.S. Application Data

[63] Continuation of Ser. No. 847,347, Mar. 9, 1992, abandoned.
[51] Int. Cl.$^6$ .............................. C12N 5/10; C12N 15/12
[52] U.S. Cl. .................. 435/252.3; 435/69.1; 435/320.1; 536/23.5
[58] Field of Search ........................ 435/69.1, 252.3, 435/320.1; 536/23.5

[56] References Cited

U.S. PATENT DOCUMENTS

| | | | |
|---|---|---|---|
| 4,578,335 | 3/1986 | Urdal et al. | 435/68 |
| 4,675,285 | 6/1987 | Clark et al. | 435/6 |
| 4,816,565 | 3/1989 | Honjo et al. | 530/351 |
| 5,116,951 | 5/1992 | Druez et al. | 530/395 |
| 5,350,683 | 9/1994 | Sims et al. | 435/69.1 |

OTHER PUBLICATIONS

Nakanishi, Science 258: 597–603, 23 Oct. 1992.
Sunahara et al, Nature 350: 614–619, 18 Apr. 1991.
Tiherl et al, PNAS 88: 7491–7495, Sep. 1991.
Van Tol et al, Nature 350: 610–614, 18 Apr. 1991.
Sims et al., "cDNA Expression Cloning of the IL-1 Receptor, a Member of the Immunoglobulin Superfamily", Science 241: 585–589 (Jul. 29, 1988).
Aruffo et al., "Molecular Cloning of a CD28 cDNA by a high efficiency COS cell expression system", Proc. Natl. Acad. Sci. USA 84: 8573–8577 (Dec. 1987).
Aggarwal et al., Human Cytokines Handbook for Basic and Chemical Research (Blackwell Scientific Publications, 1992), pp. 101 and 241.
Cell 66:1165–74, 20 Sep. 1991, Kitamura et al Expression Cloning of the Human IL-3 Receptor cDNA Reveals a Shared β Subunit . . . .
Science 241:825–28, 12 Aug. 1988, Yamasaki et al Cloning and Expression of the Human Interleukin-6 (BSF-2/IFNβ2) Receptor.
Cell:60: 945–51, 23 Mar. 1990, Goodwin et al. Cloning of the Human and Murine Interleukin-7 Receptors: Demonstration of a Soluble Form and Homology . . . .
Casman, DNA and Protein Engineering Techniques vol. 2(1) 1990, pp. 1–3.
Gerard et al, JBC 265, 1990, pp. 20455–20462.
Holmes et al., Science 253: 1278–1279 (Sep. 13, 1991).
Murphy et al., Science 253: 1280–1282 (Sep. 13, 1991).
Moseley et al., Cell 59: 335–348 (Oct. 20, 1989).
Gillis, "T–Cell Derived Lymphocytes" in Paul, ed., Fundamentals of Immunology, Second Edition (Raven Press Ltd., 1989), pp. 632–634.
Fanslow et al., Science 248: 739–741 (May 11, 1990).
Tage et al., Cell 58: 573–591 (1989).
Uyttenhove et al., Proc. Natl. Acad. Sci. 85: 6934–6938 (Sep. 1988).
Van Snick et al., J. Exp. Med. 169: 363–368 (Jan. 1989).
Donahue et al., Blood 75(12): 2271–2275 (Jun. 15, 1990).
Williams et al., Blood 76(5): 906–911 (Jan. 1990).
Halbrook et al., Blood 77(10): 2129–2134 (May 15, 1991).
Merz et al., Blood 78(5): 1311–1317 (Sep. 1, 1991).

Primary Examiner—John Ulm
Attorney, Agent, or Firm—Felfe & Lynch

[57] ABSTRACT

The invention describes nucleic acid sequences which code for the interleukin 9 receptor (IL9-R) molecule. These sequences may be used as probes to identify cells expressing the molecule, and as agents to transfect recipient cells.

23 Claims, 3 Drawing Sheets

FIG. 2

SEQUENCE LISTING ( 1 ) GENERAL INFORMATION:

( i i i ) NUMBER OF SEQUENCES: 12

( 2 ) INFORMATION FOR SEQ ID NO: 1:

( i ) SEQUENCE CHARACTERISTICS:
( A ) LENGTH: 2281 base pairs
( B ) TYPE: nucleic acid
( C ) STRANDEDNESS: single
( D ) TOPOLOGY: linear ( x i ) SEQUENCE DESCRIPTION: SEQ ID NO: 1:

| | | | | | | |
|---|---|---|---|---|---|---|
| CTCCATGGCC | CTGGGAAGAT | GCATTGCGGA | AGGTTGGACC | TTGGAGAGAG | TGGCGGTGAA | 60 |
| ACAGGTCTCC | TGGTTCCTGA | TCTACAGCTG | GGTCTGCTCT | GGAGTCTGCC | GGGGAGTCTC | 120 |
| GGTCCCAGAG | CAAGGAGGAG | GAGGGCAGAA | GGCTGGAGCA | TTCACCTGTC | TCAGCAACAG | 180 |
| TATTTACAGG | ATCGACTGCC | ACTGGTCGGC | TCCAGAGCTG | GGCCAGGAAT | CCAGGGCCTG | 240 |
| GCTCCTCTTT | ACCAGTAACC | AGGTGACTGA | AATCAAACAC | AAATGCACCT | TCTGGGACAG | 300 |
| TATGTGTACC | CTGGTGCTGC | CTAAAGAGGA | GGTGTTCTTA | CCTTTTGACA | ACTTCACCAT | 360 |
| CACACTTCAC | CGCTGCATCA | TGGGACAGGA | ACAGGTCAGC | CTGGTGGACT | CACAGTACCT | 420 |
| GCCCAGGAGA | CACATCAAGT | TGGACCCACC | CTCTGATCTG | CAGAGCAATG | TCAGCTCTGG | 480 |
| GCGTTGTGTC | CTGACCTGGG | GTATCAATCT | TGCCCTGGAG | CCATTGATCA | CATCCCTCAG | 540 |
| CTACGAGCTG | GCCTTCAAGA | GGCAGGAAGA | GGCCTGGGAG | GCCCGGCACA | AGGACCGTAT | 600 |
| CGTTGGAGTG | ACCTGGCTCA | TCCTTGAAGC | CGTCGAACTG | AATCCTGGTT | CCATCTACGA | 660 |
| GGCCAGGCTG | CGTGTCCAGA | TGACTTTGGA | GAGTTATGAG | GACAAGACAG | AGGGGGAATA | 720 |
| TTATAAGAGC | CATTGGAGTG | AGTGGAGCCA | GCCCGTGTCC | TTTCCTTCTC | CCCAGAGGAG | 780 |
| ACAGGGCCTC | CTGGTCCCAC | GCTGGCAATG | GTCAGCCAGC | ATCCTTGTAG | TTGTGCCCAT | 840 |

```
CTTTCTTCTG  CTGACTGGCT  TTGTCCACCT  TCTGTTCAAG  CTGTCACCCA  GGCTGAAGAG   900
AATCTTTTAC  CAGAACATTC  CATCTCCCGA  GGCGTTCTTC  CATCCTCTCT  ACAGTGTGTA   960
CCATGGGGAC  TTCCAGAGTT  GGACAGGGGC  CCGCAGAGCC  GGACCACAAG  CAAGACAGAA  1020
TGGTGTCAGT  ACTTCATCAG  CAGGCTCAGA  GTCCAGCATC  TGGGAGGCCG  TCGCCACACT  1080
CACCTATAGC  CCGGCATGCC  CTGTGCAGTT  TGCCTGCCTG  AAGTGGGAGG  CCACAGCCCC  1140
GGGCTTCCCA  GGGCTCCCAG  GCTCAGAGCA  TGTGCTGCCG  GCAGGGTGTC  TGGAGTTGGA  1200
AGGACAGCCA  TCTGCCTACC  TGCCCCAGGA  GGACTGGGCC  CCACTGGGCT  CTGCCAGGCC  1260
CCCTCCTCCA  GACTCAGACA  GCGGCAGCAG  CGACTATTGC  ATGTTGGACT  GCTGTGAGGA  1320
ATGCCACCTC  TCAGCCTTCC  CAGGACACAC  CGAGAGTCCT  GAGCTCACGC  TAGCTCAGCC  1380
TGTGGCCCTT  CCTGTGTCCA  GCAGGGCCTG  ACACCTACCA  AGGGATGTGG  GCATTCTCTT  1440
CCCTCCTATC  CTCGGATGGC  ACCAGACACA  GTCTCTGCGT  GTCTCTGCTA  GGTGCACCAT  1500
GTCTGTTTTG  GGGAGATGAA  CGAAAGGCCC  CAGGCTGACC  CTGGGGTGCG  TGTGGAACTC  1560
CGGAGAGGAG  GCAGCTGTGC  ACGGATCAGA  GGCAATGCGG  ATGGAAGCAG  TAGACTGTGC  1620
CTTACCCCCC  TGCTCTGCCT  TTGTGGTGGG  GATGCCTCCA  GGGTCAGCAT  CTTAACATCG  1680
CCTTCGCTTC  TCTTGTCTTT  CTGGCTCTGT  CCCAGGCCTG  AAAAAAGAAT  GTGACAAGCA  1740
GCCTGGTCTG  TTCTTCCACC  CCTAAAGGGC  TGGCCTGGGC  CCAGGGACAC  TGATGAGACA  1800
ACATTGGTGA  AGTGTCCCTT  TTCAGTGCCT  TTCCCATTAA  GACCAGAAGG  GACGCTTTTG  1860
ACTGCAGGCT  GTGGGTGGCT  GGGTACGGAG  GGAATGATGG  AGCTTTGAGC  AGGTGGGGTT  1920
GTCCATCTTT  GAGCTTTTGG  GGTTCCAAGA  TCAGCTGGAA  GGAGTCTCAC  CGACTGATTC  1980
AAAGAAGTCT  TACCCATCTG  TGATATTTTC  TTTCCTGGTG  CCGTGATAAA  ACACCGTGAC  2040
CAAAAATGAC  TTACAAAAGG  AAGAGTTGGC  TTGGTTTAAG  GTTCCAGAGG  TGTGGAGACA  2100
TGGCAGCCAG  CGGCACACAT  GGCAGTGAGG  ACAGGAAGCT  GAGAGCTCAC  ATCTCAACCA  2160
AAAGTTGAGT  GAACTGAAAG  TACTATCCCC  TCCCCACCC   CAACTCCAGC  AAGGCTCCAC  2220
CCCCCTGAAG  GTTCCATGCC  TCCCTAAACA  GCTCGGCCAA  ATAGAGACCA  AGTGTTCAAA  2280
T                                                                      2281
```

( 2 ) INFORMATION FOR SEQ ID NO: 2:

( i ) SEQUENCE CHARACTERISTICS:
        ( A ) LENGTH: 1905 base pairs
        ( B ) TYPE: nucleic acid
        ( C ) STRANDEDNESS: single
        ( D ) TOPOLOGY: linear ( x i ) SEQUENCE DESCRIPTION: SEQ ID NO: 2:

```
CACCTCCTGG  CTGGGGCTGC  CTGAGACTCT  CCATGGCCCT  GGGAAGATGC  ATTGCGGAAG    60
GTTGGACCTT  GGAGAGAGTG  GCGGTGAAAC  AGGTCTCCTG  GTTCCTGATC  TACAGCTGGG   120
TCTGCTCTGG  AGTCTGCCGG  GGAGTCTCGG  TCCCAGAGCA  AGGAGGAGGA  GGGCAGAAGG   180
CTGGAGCATT  CACCTGTCTC  AGCAACAGTA  TTTACAGGAT  CGACTGCCAC  TGGTCGGCTC   240
CAGAGCTGGG  CCAGGAATCC  AGGGCCTGGC  TCCTCTTTAC  CAGTAACCAG  GTGACTGAAA   300
TCAAACACAA  ATGCACCTTC  TGGGACAGTA  TGTGTACCCT  GGTGCTGCCT  AAAGAGGAGG   360
TGTTCTTACC  TTTTGACAAC  TTCACCATCA  CACTTCACCG  CTGCATCATG  GGACAGGAAC   420
AGGTCAGCCT  GGTGGACTCA  CAGTACCTGC  CAGGAGACA   CATCAAGTTG  GACCCACCCT   480
CTGATCTGCA  GAGCAATGTC  AGCTCTGGGC  GTTGTGTCCT  GACCTGGGGT  ATCAATCTTG   540
```

| | | | | | |
|---|---|---|---|---|---|
| CCCTGGAGCC | ATTGATCACA | TCCCTCAGCT | ACGAGCTGGC | CTTCAAGAGG | CAGGAAGAGG | 600 |
| CCTGGGAGCA | GGCCCGGCAC | AAGGACCGTA | TCGTTGGAGT | GACCTGGCTC | ATCCTTGAAG | 660 |
| CCGTCGAACT | GAATCCTGGT | TCCATCTACG | AGGCCAGGCT | GCGTGTCCAG | ATGACTTTGG | 720 |
| AGAGTTATGA | GGACAAGACA | GAGGGGGAAT | ATTATAAGAG | CCATTGGAGT | GAGTGGAGCC | 780 |
| AGCCCGTGTC | CTTTCCTTCT | CCCCAGAGGA | GACAGGGCCT | CCTGGTCCCA | CGCTGGCAAT | 840 |
| GGTCAGCCAG | CATCCTTGTA | GTTGTGCCCA | TCTTCTTCT | GCTGACTGGC | TTTGTCCACC | 900 |
| TTCTGTTCAA | GCTGTCACCC | AGGCTGAAGA | GAATCTTTTA | CCAGAACATT | CCATCTCCG | 960 |
| AGGCGTTCTT | CCATCCTCTC | TACAGTGTGT | ACCATGGGGA | CTTCCAGAGT | TGGACAGGGG | 1020 |
| CCCGCAGAGC | CGGACCACAA | GCAAGACAGA | ATGGTGTCAG | TACTTCATCA | GCAGGCTCAG | 1080 |
| AGTCCAGCAT | CTGGGAGGCC | GTCGCCACAC | TCACCTATAG | CCCGGCATGC | CCTGTGCAGT | 1140 |
| TTGCCTGCCT | GAAGTGGGAG | GCCACAGCGT | GAGAAGGGAC | AGCCAGCCAC | TCAGTGCGTG | 1200 |
| GGCTTAGATT | GGGAAGAGAC | CTCCCAAGCA | GCTTCCCCTC | CTCCCCAGCC | CCTGCCATTC | 1260 |
| ACCCCTGCTG | GCCGTCCATC | CCCAGGATCC | ACTGTGGAGC | CAAGCCCACA | GACCCGGCCT | 1320 |
| GATTCAGCTC | TGACACTCGC | TGCGCTGCTC | CGTTGTGAAC | TTTGGCCAAG | TCACCACTTT | 1380 |
| TACCTCAGCT | TCCTCCTGTG | AGAACAGGGT | TGCCTTAGAG | TTGCCTAATC | CCTAAGGAGA | 1440 |
| CTGAGACAAA | CTTGTCTGCA | AATATCTATC | CGATGTATAT | TGTTAGGAGC | TCGAGGGTCC | 1500 |
| GTGGGTGGGC | GGGGCAGGGG | GGTGGGGATG | CGGTTGGCGC | ATATCACTGT | GTCAACAGCC | 1560 |
| AGAGCCTTCC | TCCATGTCTC | AACCAACACT | CTCCAAGCTG | AATTCTCAGG | CTGAACTCAC | 1620 |
| TGTCACCTGT | GAAGTAAACC | CCGGCAGACC | TGGAAGATTG | GTGGTAGGAT | TGTGGAGGTT | 1680 |
| GCAGGGAGCA | TGCTCAGTGG | GCACTAGTTG | CCTGCTGGGT | ACCAGGAGAT | GCTTGTGCCC | 1740 |
| TGAGGTATCT | TTAAGAACTA | TCACGGAATT | GGACTGGGAG | CTCAGGAGAG | AGCTTGGTAG | 1800 |
| ACTGGCAGTG | TCAGTGAAAC | AGTTATTTAG | CCAAGAACAA | CATTCCTGGG | GCTGGGACA | 1860 |
| GTGGCTCGGT | GAAACCAACC | TGGAACATGG | GAGGTTGTAA | GTTCG | | 1905 |

( 2 ) INFORMATION FOR SEQ ID NO: 3:

( i ) SEQUENCE CHARACTERISTICS:
        ( A ) LENGTH: 1214 base pairs
        ( B ) TYPE: nucleic acid
        ( C ) STRANDEDNESS: single
        ( D ) TOPOLOGY: linear ( x i ) SEQUENCE DESCRIPTION: SEQ ID NO: 3:

| | | | | | |
|---|---|---|---|---|---|
| ATGGCCCTGG | GAAGATGCAT | TGCGGAAGGT | TGGACCTTGG | AGAGAGTGGC | GGTGAAACAG | 60 |
| GTCTCCTGGT | TCCTGATCTA | CAGCTGGGTC | TGCTCTGGAG | TCTGCCGGGG | AGTCTCGGTC | 120 |
| CCAGAGCAAG | GAGGAGGAGG | GCAGAAGGCT | GGAGCATTCA | CCTGTCTCAG | CAACAGTATT | 180 |
| TACAGGATCG | ACTGCCACTG | GTCGGCTCCA | GAGCTGGGCC | AGGAATCCAG | GGCCTGGCTC | 240 |
| CTCTTTACCA | GTAACCAGGT | GACTGAAATC | AAACACAAAT | GCACCTTCTG | GGACAGTATG | 300 |
| TGTACCCTGG | TGCTGCCTAA | AGAGGAGGTG | TTCTTACCTT | TTGACAACTT | CACCATCACA | 360 |
| CTTCACCGCT | GCATCATGGG | ACAGGAACAG | GTCAGCCTGG | TGGACTCACA | GTACCTGCCC | 420 |
| AGGAGACACA | TCAAGTTGGA | CCCACCCTCT | GATCTGCAGA | GCAATGTCAG | CTCTGGGCGT | 480 |
| TGTGTCCTGA | CCTGGGGTAT | CAATCTTGCC | CTGGAGCCAT | TGATCACATC | CCTCAGCTAC | 540 |
| GAGCTGGCCT | TCAAGAGGCA | GGAAGAGGCC | TGGGAGCAGG | CCCGGCACAA | GGACCGTATC | 600 |
| GTTGGAGTGA | CCTGGCTCAT | CCTTGAAGCC | GTCGAACTGA | ATCCTGAAAA | AGAATGTGA | 660 |
| CAAGCAGCCT | GGTCTGTTCT | TCCACCCCTA | AAGGGCTGGC | CTGGGCCCAG | GGACACTGAT | 720 |

| | | | | | |
|---|---|---|---|---|---|
| GAGACAACAT | TGGTGAAGTG | TCCCTTTTCA | GTGCCTTTCC | CATTAAGACC | AGAAGGGACG | 780 |
| CTTTTGACTG | CAGGCTGTGG | GTGGCTGGGT | ACGGAGGGAA | TGATGGAGCT | TTGAGCAGGT | 840 |
| GGGGTTGTCC | ATCTTTGAGC | TTTTGGGTTC | CAAGATCAGC | TGGAAGGAGT | CTCACCGACT | 900 |
| GATTCAAAGA | AGTCTTACCC | ATCTGTGATA | TTTTCTTTCC | TGGTGCCGTG | ATAAACACC | 960 |
| GTGACCAAAA | ATGACTTACA | AAAGGAAGAG | TTGGCTTGGT | TTAAGGTTCC | AGAGGTGTGG | 1020 |
| AGACATGGCA | GCCAGCGGCA | CACATGGCAG | TGAGGACAGG | AAGCTGAGAG | CTCACATCTC | 1080 |
| AACCAAAAGT | TGAGTGAACT | GAAAGTACTA | TCCCCTCCCC | CACCCCAACT | CCAGCAAGGC | 1140 |
| TCCACCCCCC | TGAAGGTTCC | ATGCCTCCCT | AAACAGCTCG | GCCAAATAGA | GACCAAGTGT | 1200 |
| TCAAATAAAA | AAAA | | | | | 1214 |

( 2 ) INFORMATION FOR SEQ ID NO: 4:

( i ) SEQUENCE CHARACTERISTICS:
( A ) LENGTH: 1947 base pairs
( B ) TYPE: nucleic acid
( C ) STRANDEDNESS: single
( D ) TOPOLOGY: linear ( x i ) SEQUENCE DESCRIPTION: SEQ ID NO: 4:

| | | | | | |
|---|---|---|---|---|---|
| AGCAGCTCTG | TAATGCGCTT | GTGGTTTCAG | ATGTGGGCGG | CCTGTGTGAA | CCTGTCGTGC | 60 |
| AAAGCTCACG | TCACCAACTG | CTGCAGTTAT | CTCCTGAATC | AGGCTGAGGG | TCTTTGCTGT | 120 |
| GCACCCAGAG | ATAGTTGGGT | GACAAATCAC | CTCCAGGTTG | GGGATGCCTC | AGACTTGTGA | 180 |
| TGGGACTGGG | CAGATGCATC | TGGGAAGGCT | GGACCTTGGA | GAGTGAGGCC | CTGAGGCGAG | 240 |
| ACATGGGCAC | CTGGCTCCTG | GCCTGCATCT | GCATCTGCAC | CTGTGTCTGC | TTGGGAGTCT | 300 |
| CTGTCACAGG | GGAAGGACAA | GGGCCAAGGT | CTAGAACCTT | CACCTGCCTC | ACCAACAACA | 360 |
| TTCTCAGGAT | CGATTGCCAC | TGGTCTGCCC | CAGAGCTGGG | ACAGGGCTCC | AGCCCTGGC | 420 |
| TCCTCTTCAC | CAGCAACCAG | GCTCCTGGCG | GCACACATAA | GTGCATCTTG | CGGGGCAGTG | 480 |
| AGTGCACCGT | CGTGCTGCCA | CCTGAGGCAG | TGCTCGTGCC | ATCTGACAAT | TTCACCATCA | 540 |
| CTTTCCACCA | CTGCATGTCT | GGGAGGGAGC | AGGTCAGCCT | GGTGGACCCG | GAGTACCTGC | 600 |
| CCCGGAGACA | CGTTAAGCTG | GACCCGCCCT | CTGACTTGCA | GAGCAACATC | AGTTCTGGCC | 660 |
| ACTGCATCCT | GACCTGGAGC | ATCAGTCCTG | CCTTGGAGCC | AATGACCACA | CTTCTCAGCT | 720 |
| ATGAGCTGGC | CTTCAAGAAG | CAGGAAGAGG | CCTGGGAGCA | GGCCCAGCAC | AGGGATCACA | 780 |
| TTGTCGGGGT | GACCTGGCTT | ATACTTGAAG | CCTTTGAGCT | GGACCCTGGC | TTTATCCATG | 840 |
| AGGCCAGGCT | GCGTGTCCAG | ATGGCCACAC | TGGAGGATGA | TGTGGTAGAG | GAGGAGCGTT | 900 |
| ATACAGGCCA | GTGGAGTGAG | TGGAGCCAGC | CTGTGTGCTT | CCAGGCTCCC | CAGAGACAAG | 960 |
| GCCCTCTGAT | CCCACCCTGG | GGGTGGCCAG | GCAACACCCT | TGTTGCTGTG | TCCATCTTTC | 1020 |
| TCCTGCTGAC | TGGCCCGACC | TACCTCCTGT | TCAAGCTGTC | GCCCAGGGTG | AAGAGAATCT | 1080 |
| TCTACCAGAA | CGTGCCCTCT | CCAGCGATGT | TCTTCCAGCC | CCTCTACAGT | GTACACAATG | 1140 |
| GGAACTTCCA | GACTTGGATG | GGGGCCCACA | GGGCCGGTGT | GCTGTTGAGC | CAGGACTGTG | 1200 |
| CTGGCACCCC | ACAGGGAGCC | TTGGAGCCCT | GCGTCCAGGA | GGCCACTGCA | CTGCTCACTT | 1260 |
| GTGGCCCAGC | GCGTCCTTGG | AAATCTGTGG | CCCTGGAGGA | GGAACAGGAG | GGCCCTGGA | 1320 |
| CCAGGCTCCC | GGGGAACCTG | AGCTCAGAGG | ATGTGCTGCC | AGCAGGGTGT | ACGGAGTGGA | 1380 |
| GGGTACAGAC | GCTTGCCTAT | CTGCCACAGG | AGGACTGGGC | CCCACGTCC | CTGACTAGGC | 1440 |
| CGGCTCCCCC | AGACTCAGAG | GGCAGCAGGA | GCAGCAGCAG | CAGCAGCAGC | AGCAGCAACA | 1500 |

-continued

| | | | | | |
|---|---|---|---|---|---|
| ACAACAACTA | CTGTGCCTTG | GGCTGCTATG | GGGGATGGCA | CCTCTCAGCC | CTCCCAGGAA | 1560 |
| ACACACAGAG | CTCTGGGCCC | ATCCCAGCCC | TGGCCTGTGG | CCTTTCTTGT | GACCATCAGG | 1620 |
| GCCTGGAGAC | CCAGCAAGGA | GTTGCCTGGG | TGCTGGCTGG | TCACTGCCAG | AGGCCTGGGC | 1680 |
| TGCATGAGGA | CCTCCAGGGC | ATGTTGCTCC | CTTCTGTCCT | CAGCAAGGCT | CGGTCCTGGA | 1740 |
| CATTCTAGGT | CCCTGACTCG | CCAGATGCAT | CATGTCCATT | TTGGGAAAAT | GGACTGAAGT | 1800 |
| TTCTGGAGCC | CTTGTCTGAG | ACTGAACCTC | CTGAGAAGGG | GCCCCTAGCA | GCGGTCAGAG | 1860 |
| GTCCTGTCTG | GATGGAGGCT | GGAGGCTCCC | CCCTCAACCC | CTCTGCTCAG | TGCCTGTGGG | 1920 |
| GAGCAGCCTC | TACCCTCAGC | ATCCTGG | | | | 1947 |

( 2 ) INFORMATION FOR SEQ ID NO: 5:

( i ) SEQUENCE CHARACTERISTICS:
        ( A ) LENGTH: 1683 base pairs
        ( B ) TYPE: nucleic acid
        ( C ) STRANDEDNESS: single
        ( D ) TOPOLOGY: linear ( x i ) SEQUENCE DESCRIPTION: SEQ ID NO: 5:

| | | | | | |
|---|---|---|---|---|---|
| ATGGGACTGG | GCAGATGCAT | CTGGGAAGGC | TGGACCTTGG | AGAGTGAGGC | CCTGAGGCGA | 60 |
| GACATGGGCA | CCTGGCTCCT | GGCCTGCATC | TGCATCTGCA | CCTGTGTCTG | CTTGGGAGTC | 120 |
| TCTGTCACAG | GGGAAGGACA | AGGGCCAAGG | TCTAGAACCT | TCACCTGCCT | CACCAACAAC | 180 |
| ATTCTCAGGA | TCGATTGCCA | CTGGTCTGCC | CCAGAGCTGG | GACAGGGCTC | CAGCCCCTGG | 240 |
| CTCCTCTTCA | CCAGCAACCA | GGCTCCTGGC | GCACACATA | AGTGCATCTT | GCGGGGCAGT | 300 |
| GAGTGCACCG | TCGTGCTGCC | ACCTGAGGCA | GTGCTCGTGC | CATCTGACAA | TTTCACCATC | 360 |
| ACTTTCCACC | ACTGCATGTC | TGGGAGGGAG | CAGGTCAGCC | TGGTGGACCC | GGAGTACCTG | 420 |
| CCCCGGAGAC | ACGTTAAGCT | GGACCCGCCC | TCTGACTTGC | AGAGCAACAT | CAGTTCTGGC | 480 |
| CACTGCATCC | TGACCTGGAG | CATCAGTCCT | GCCTTGGAGC | CAATGACCAC | ACTTCTCAGC | 540 |
| TATGAGCTGG | CCTTCAAGAA | GCAGGAAGAG | GCCTGGGAGC | AGGCCCAGCA | CAGGGATCAC | 600 |
| ATTGTCGGGG | TGACCTGGCT | TATACTTGAA | GCCTTTGAGC | TGGACCCTGG | CTTTATCCAT | 660 |
| GAGGCCAGGC | TGCGTGTCCA | GATGGCCACA | CTGGAGGATG | ATGTGGTAGA | GGAGGAGCGT | 720 |
| TATACAGGCC | AGTGGAGTGA | GTGGAGCCAG | CCTGTGTGCT | TCCAGGCTCC | CCAGAGACAA | 780 |
| GGCCCTCTGA | TCCCACCCTG | GGGGTGGCCA | GGCAACACCC | TTGTTGCTGT | GTCCATCTTT | 840 |
| CTCCTGCTGA | CTGGCCCGAC | CTACCTCCTG | TTCAAGCTGT | CGCCCAGACT | GGATGGGGG | 900 |
| CCCACAGGGC | CGGTGTGCTG | TTGAGCCAGG | ACTGTGCTGG | CACCCCACAG | GGAGCCTTGG | 960 |
| AGCCCTGCGT | CCAGGAGGCC | ACTGCACTGC | TCACTTGTGG | CCCAGCGCGT | CCTTGGAAAT | 1020 |
| CTGTGGCCCT | GGAGGAGGAA | CAGGAGGGCC | CTGGGACCAG | GCTCCGGGG | AACCTGAGCT | 1080 |
| CAGAGGATGT | GCTGCCAGCA | GGGTGTACGG | AGTGGAGGGT | ACAGACGCTT | GCCTATCTGC | 1140 |
| CACAGGAGGA | CTGGGCCCCC | ACGTCCCTGA | CTAGGCCGGC | TCCCCAGAC | TCAGAGGGCA | 1200 |
| GCAGGAGCAG | CAGCAGCAGC | AGCAGCAGCA | GCAACAACAA | CAACTACTGT | GCCTTGGGCT | 1260 |
| GCTATGGGGG | ATGGCACCTC | TCAGCCCTCC | CAGGAAACAC | ACAGAGCTCT | GGGCCCATCC | 1320 |
| CAGCCCTGGC | CTGTGGCCTT | TCTTGTGACC | ATCAGGGCCT | GGAGACCCAG | CAAGGAGTTG | 1380 |
| CCTGGGTGCT | GGCTGGTCAC | TGCCAGAGGC | CTGGGCTGCA | TGAGGACCTC | CAGGGCATGT | 1440 |
| TGCTCCCTTC | TGTCCTCAGC | AAGGCTCGGT | CCTGGACATT | CTAGGTCCCT | GACTCGCCAG | 1500 |
| ATGCATCATG | TCCATTTTGG | GAAAATGGAC | TGAAGTTTCT | GGAGCCCTTG | TCTGAGACTG | 1560 |
| AACCTCCTGA | GAAGGGGCCC | CTAGCAGCGG | TCAGAGGTCC | TGTCTGGATG | GAGGCTGGAG | 1620 |

-continued

| | | | | | |
|---|---|---|---|---|---|
| GCTCCCCCCT | CAACCCCTCT | GCTCAGTGCC | TGTGGGGAGC | AGCCTCTACC | CTCAGCATCC | 1680 |
| TGG | | | | | | 1683 |

( 2 ) INFORMATION FOR SEQ ID NO: 6:

( i ) SEQUENCE CHARACTERISTICS:
        ( A ) LENGTH: 1997 base pairs
        ( B ) TYPE: nucleic acid
        ( C ) STRANDEDNESS: single
        ( D ) TOPOLOGY: linear ( x i ) SEQUENCE DESCRIPTION: SEQ ID NO: 6:

| | | | | | |
|---|---|---|---|---|---|
| CCAGGTTGGG | GATGCCTCAG | ACTTGTGATG | GGACTGGGCA | GATGCATCTG | GGAAGGTCCT | 60 |
| GGTGGTGACT | CCAACCCTGC | CCTCACATAT | CCCAAGAGCA | GCTGACTGCG | CTTCCCCATT | 120 |
| CCCACCTTTC | CAGTAACTGC | TGCAAGAACG | GACAGACACT | GCTGCAGAGA | ACTTGCCACG | 180 |
| GTGTTTCATG | CTGTGGCTGG | TGGTTCCAGG | CTGCACGCTC | CATTCTAGGA | AAGGGGCCCT | 240 |
| CAGCCAGTCC | CTTGCAGGCT | GGACCTTGGA | GAGTGAGGCC | CTGAGGCGAG | ACATGGGCAC | 300 |
| CTGGCTCCTG | GCCTGCATCT | GCATCTGCAC | CTGTGTCTGC | TTGGGAGTCT | CTGTCACAGG | 360 |
| GGAAGGACAA | GGGCCAAGGT | CTAGAACCTT | CACCTGCCTC | ACCAACAACA | TTCTCAGGAT | 420 |
| CGATTGCCAC | TGGTCTGCCC | CAGAGCTGGG | ACAGGGCTCC | AGCCCTGGC | TCCTCTTCAC | 480 |
| CAGCAACCAG | GCTCCTGGCG | GCACACATAA | GTGCATCTTG | CGGGGCAGTG | AGTGCACCGT | 540 |
| CGTGCTGCCA | CCTGAGGCAG | TGCTCGTGCC | ATCTGACAAT | TCACCATCA | CTTTCCACCA | 600 |
| CTGCATGTCT | GGGAGGGAGC | AGGTCAGCCT | GGTGGACCCG | GAGTACCTGC | CCCGGAGACA | 660 |
| CGTTAAGCTG | GACCCGCCCT | CTGACTTGCA | GAGCAACATC | AGTTCTGGCC | ACTGCATCCT | 720 |
| GACCTGGAGC | ATCAGTCCTG | CCTTGGAGCC | AATGACCACA | CTTCTCAGCT | ATGAGCTGGC | 780 |
| CTTCAAGAAG | CAGGAAGAGG | CCTGGGAGCA | GGCCCAGCAC | AGGGATCACA | TTGTCGGGGT | 840 |
| GACCTGGCTT | ATACTTGAAG | CCTTTGAGCT | GGACCCTGGC | TTTATCCATG | AGGCCAGGCT | 900 |
| GCGTGTCCAG | ATGGCCACAC | TGGAGGATGA | TGTGGTAGAG | GAGGAGCGTT | ATACAGGCCA | 960 |
| GTGGAGTGAG | TGGAGCCAGC | CTGTGTGCTT | CCAGGCTCCC | CAGAGACAAG | GCCCTCTGAT | 1020 |
| CCCACCCTGG | GGGTGGCCAG | GCAACACCCT | TGTTGCTGTG | TCCATCTTTC | TCCTGCTGAC | 1080 |
| TGGCCCGACC | TACCTCCTGT | TCAAGCTGTC | GCCCAGGGTG | AAGAGAATCT | TCTACCAGAA | 1140 |
| CGTGCCCTCT | CCAGCGATGT | TCTTCCAGCC | CCTCTACAGT | GTACACAATG | GGAACTTCCA | 1200 |
| GACTTGGATG | GGGGCCCACA | GGGCCGGTGT | GCTGTTGAGC | CAGGACTGTG | CTGGCACCCC | 1260 |
| ACAGGGAGCC | TTGGAGCCCT | GCGTCCAGGA | GGCCACTGCA | CTGCTCACTT | GTGGCCCAGC | 1320 |
| GCGTCCTTGG | AAATCTGTGG | CCCTGGAGGA | GGAACAGGAG | GGCCCTGGGA | CCAGGCTCCC | 1380 |
| GGGGAACCTG | AGCTCAGAGG | ATGTGCTGCC | AGCAGGGTGT | ACGGAGTGGA | GGGTACAGAC | 1440 |
| GCTTGCCTAT | CTGCCACAGG | AGGACTGGGC | CCCCACGTCC | CTGACTAGGC | CGGCTCCCCC | 1500 |
| AGACTCAGAG | GGCAGCAGGA | GCAGCAGCAG | CAGCAGCAGC | AGCAGCAACA | ACAACAACTA | 1560 |
| CTGTGCCTTG | GGCTGCTATG | GGGGATGGCA | CCTCTCAGCC | CTCCCAGGAA | ACACACAGAG | 1620 |
| CTCTGGGCCC | ATCCCAGCCC | TGGCCTGTGG | CCTTTCTTGT | GACCATCAGG | GCCTGGAGAC | 1680 |
| CCAGCAAGGA | GTTGCCTGGG | TGCTGGCTGG | TCACTGCCAG | AGGCCTGGGC | TGCATGAGGA | 1740 |
| CCTCCAGGGC | ATGTTGCTCC | CTTCTGTCCT | CAGCAAGGCT | CGGTCCTGGA | CATTCTAGGT | 1800 |
| CCCTGACTCG | CCAGATGCAT | CATGTCCATT | TTGGGAAAAT | GGACTGAAGT | TTCTGGAGCC | 1860 |
| CTTGTCTGAG | ACTGAACCTC | CTGAGAAGGG | GCCCCTAGCA | GCGGTCAGAG | GTCCTGTCTG | 1920 |

```
GATGGAGGCT GGAGGCTCCC CCCTCAACCC CTCTGCTCAG TGCCTGTGGG GAGCAGCCTC    1980
TACCCTCAGC ATCCTGG                                                  1997
```

( 2 ) INFORMATION FOR SEQ ID NO: 7:

( i ) SEQUENCE CHARACTERISTICS:
    ( A ) LENGTH: 468 amino acid residues
    ( B ) TYPE: amino acid
    ( D ) TOPOLOGY: linear ( x i ) SEQUENCE DESCRIPTION: SEQ ID NO: 7:

```
Met  Ala  Leu  Gly  Arg  Cys  Ile  Ala  Glu  Gly  Trp  Thr  Leu  Glu  Arg  Val
               5                    10                       15
Ala  Val  Lys  Gln  Val  Ser  Trp  Phe  Leu  Ile  Tyr  Ser  Trp  Val  Cys  Ser
          20                        25                  30
Gly  Val  Cys  Arg  Gly  Val  Ser  Val  Pro  Glu  Gln  Gly  Gly  Gly  Gly  Gln
               35                        40                       45
Lys  Ala  Gly  Ala  Phe  Thr  Cys  Leu  Ser  Asn  Ser  Ile  Tyr  Arg  Ile  Asp
          50                    55                       60
Cys  His  Trp  Ser  Ala  Pro  Glu  Leu  Gly  Gln  Glu  Ser  Arg  Ala  Trp  Leu
65                       70                       75                        80
Leu  Phe  Thr  Ser  Asn  Gln  Val  Thr  Glu  Ile  Lys  His  Lys  Cys  Thr  Phe
                    85                       90                  95
Trp  Asp  Ser  Met  Cys  Thr  Leu  Val  Leu  Pro  Phe  Glu  Glu  Val  Phe  Leu
                    100                      105                      110
Pro  Phe  Asp  Asn  Phe  Thr  Ile  Thr  Leu  His  Arg  Cys  Ile  Met  Gly  Gln
               115                      120                 125
Glu  Gln  Val  Ser  Leu  Val  Asp  Ser  Gln  Tyr  Leu  Pro  Arg  Arg  His  Ile
     130                      135                      140
Lys  Leu  Asp  Pro  Pro  Ser  Asp  Leu  Gln  Ser  Asn  Val  Ser  Ser  Gly  Arg
145                           150                      155                 160
Cys  Val  Leu  Thr  Trp  Gly  Ile  Asn  Leu  Ala  Leu  Glu  Pro  Leu  Ile  Thr
               165                      170                      175
Ser  Leu  Ser  Tyr  Glu  Leu  Ala  Phe  Lys  Arg  Gln  Glu  Glu  Ala  Trp  Glu
               180                      185                 190
Ala  Arg  His  Lys  Asp  Arg  Ile  Val  Gly  Val  Thr  Trp  Leu  Ile  Leu  Glu
          195                      200                      205
Ala  Val  Glu  Leu  Asn  Pro  Gly  Ser  Ile  Tyr  Glu  Ala  Arg  Leu  Arg  Val
     210                      215                 220
Gln  Met  Thr  Leu  Glu  Ser  Tyr  Glu  Asp  Lys  Thr  Glu  Gly  Glu  Tyr  Tyr
225                      230                      235                      240
Lys  Ser  His  Trp  Ser  Glu  Trp  Ser  Gln  Pro  Val  Ser  Phe  Pro  Ser  Pro
               245                      250                 255
Gln  Arg  Arg  Gln  Gly  Leu  Leu  Val  Pro  Arg  Trp  Gln  Trp  Ser  Ala  Ser
               260                      265                 270
Ile  Leu  Val  Val  Val  Pro  Ile  Phe  Leu  leu  Leu  Thr  Gly  Phe  Val  His
          275                      280                 285
Leu  Leu  Phe  Lys  Leu  Ser  Pro  Arg  Leu  Lys  Arg  Ile  Phe  Tyr  Gln  Asn
     290                      295                 300
Ile  Pro  Ser  Pro  Glu  Ala  Phe  Phe  His  Pro  Leu  Tyr  Ser  Val  Tyr  His
305                      310                      315                      320
Gly  Asp  Phe  Gln  Ser  Trp  Thr  Gly  Ala  Arg  Arg  Ala  Gly  Pro  Gln  Ala
               325                      330                      335
Arg  Gln  Asn  Gly  Val  Ser  Thr  Ser  Ser  Ala  Gly  Ser  Glu  Ser  Ser  Ile
               340                      345                      350
```

-continued

| | | | | | | | | | | | | | | |
|---|---|---|---|---|---|---|---|---|---|---|---|---|---|---|
| Trp | Glu | Ala | Val | Ala | Thr | Leu | Thr | Tyr | Ser | Pro | Ala | Cys | Pro | Val | Gln |
| | | 355 | | | | | 360 | | | | | 365 | | | |
| Phe | Ala | Cys | Leu | Lys | Trp | Glu | Ala | Thr | Ala | Pro | Gly | Phe | Pro | Gly | Leu |
| | 370 | | | | 375 | | | | | 380 | | | | | |
| Pro | Gly | Ser | Glu | His | Val | Leu | Pro | Ala | Gly | Cys | Leu | Glu | Leu | Glu | Gly |
| 385 | | | | | 390 | | | | | 395 | | | | | 400 |
| Gln | Pro | Ser | Ala | Tyr | Leu | Pro | Gln | Glu | Asp | Trp | Ala | Pro | Leu | Gly | Ser |
| | | | | 405 | | | | | 410 | | | | | 415 | |
| Ala | Arg | Pro | Pro | Pro | Asp | Ser | Asp | Ser | Gly | Ser | Ser | Asp | Tyr | Cys |
| | | | 420 | | | | | 425 | | | | | 430 | | |
| Met | Leu | Asp | Cys | Cys | Glu | Glu | Cys | His | Leu | Ser | Ala | Phe | Pro | Gly | His |
| | | 435 | | | | | 440 | | | | | 445 | | | |
| Thr | Glu | Ser | Pro | Glu | Leu | Thr | Leu | Ala | Gln | Pro | Val | Ala | Leu | Pro | Val |
| | 450 | | | | | 455 | | | | | 460 | | | | |
| Ser | Ser | Arg | Ala |
| 465 | | | |

( 2 ) INFORMATION FOR SEQ ID NO: 8:

( i ) SEQUENCE CHARACTERISTICS:
( A ) LENGTH: 379 amino acid residues
( B ) TYPE: amino acid
( D ) TOPOLOGY: linear ( x i ) SEQUENCE DESCRIPTION: SEQ ID NO: 8:

| | | | | | | | | | | | | | | | |
|---|---|---|---|---|---|---|---|---|---|---|---|---|---|---|---|
| Met | Ala | Leu | Gly | Arg | Cys | Ile | Ala | Glu | Gly | Trp | Thr | Leu | Glu | Arg | Val |
| | | | | 5 | | | | | 10 | | | | | 15 | |
| Ala | Val | Lys | Gln | Val | Ser | Trp | Phe | Leu | Ile | Tyr | Ser | Trp | Val | Cys | Ser |
| | | | 20 | | | | | 25 | | | | | 30 | | |
| Gly | Val | Cys | Arg | Gly | Val | Ser | Val | Pro | Glu | Gln | Gly | Gly | Gly | Gly | Gln |
| | | 35 | | | | | 40 | | | | | 45 | | | |
| Lys | Ala | Gly | Ala | Phe | Thr | Cys | Leu | Ser | Asn | Ser | Ile | Tyr | Arg | Ile | Asp |
| | 50 | | | | | 55 | | | | | 60 | | | | |
| Cys | His | Trp | Ser | Ala | Pro | Glu | Leu | Gly | Gln | Glu | Ser | Arg | Ala | Trp | Leu |
| 65 | | | | | 70 | | | | | 75 | | | | | 80 |
| Leu | Phe | Thr | Ser | Asn | Gln | Val | Thr | Glu | Ile | Lys | His | Lys | Cys | Thr | Phe |
| | | | | 85 | | | | | 90 | | | | | 95 | |
| Trp | Asp | Ser | Met | Cys | Thr | Leu | Val | Leu | Pro | Phe | Glu | Glu | Val | Phe | Leu |
| | | | 100 | | | | | 105 | | | | | 110 | | |
| Pro | Phe | Asp | Asn | Phe | Thr | Ile | Thr | Leu | His | Arg | Cys | Ile | Met | Gly | Gln |
| | | 115 | | | | | 120 | | | | | 125 | | | |
| Glu | Gln | Val | Ser | Leu | Val | Asp | Ser | Gln | Tyr | Leu | Pro | Arg | Arg | His | Ile |
| | 130 | | | | | 135 | | | | | 140 | | | | |
| Lys | Leu | Asp | Pro | Pro | Ser | Asp | Leu | Gln | Ser | Asn | Val | Ser | Ser | Gly | Arg |
| 145 | | | | | 150 | | | | | 155 | | | | | 160 |
| Cys | Val | Leu | Thr | Trp | Gly | Ile | Asn | Leu | Ala | Leu | Glu | Pro | Leu | Ile | Thr |
| | | | | 165 | | | | | 170 | | | | | 175 | |
| Ser | Leu | Ser | Tyr | Glu | Leu | Ala | Phe | Lys | Arg | Gln | Glu | Glu | Ala | Trp | Glu |
| | | | 180 | | | | | 185 | | | | | 190 | | |
| Gln | Ala | Arg | His | Lys | Asp | Arg | Ile | Val | Gly | Val | Thr | Trp | Leu | Ile | Leu |
| | | 195 | | | | | 200 | | | | | 205 | | | |
| Glu | Ala | Val | Glu | Leu | Asn | Pro | Gly | Ser | Ile | Tyr | Glu | Ala | Arg | Leu | Arg |
| | 210 | | | | | 215 | | | | | 220 | | | | |
| Val | Gln | Met | Thr | Leu | Glu | Ser | Tyr | Glu | Asp | Lys | Thr | Glu | Gly | Glu | Tyr |
| 225 | | | | | 230 | | | | | 235 | | | | | 240 |
| Tyr | Lys | Ser | His | Trp | Ser | Glu | Trp | Ser | Gln | Pro | Val | Ser | Phe | Pro | Ser |

|  |  |  | 245 |  |  |  |  | 250 |  |  |  | 255 |  |  |
|---|---|---|---|---|---|---|---|---|---|---|---|---|---|---|

Pro Gln Arg Arg Gln Gly Leu Leu Val Pro Arg Trp Gln Trp Ser Ala
            260                 265             270

Ser Ile Leu Val Val Val Pro Ile Phe Leu Leu Leu Thr Gly Phe Val
        275             280                 285

His Leu Leu Phe Lys Leu Ser Pro Arg Leu Lys Arg Ile Phe Tyr Gln
    290             295             300

Asn Ile Pro Ser Pro Glu Ala Phe Phe His Pro Leu Tyr Ser Val Tyr
305             310             315                     320

His Gly Asp Phe Gln Ser Trp Thr Gly Ala Arg Arg Ala Gly Pro Gln
            325             330             335

Ala Arg Gln Asn Gly Val Ser Thr Ser Ser Ala Gly Ser Glu Ser Ser
            340             345             350

Ile Trp Glu Ala Val Ala Thr Leu Thr Tyr Ser Pro Ala Cys Pro Val
        355             360             365

Gln Phe Ala Cys Leu Lys Trp Glu Ala Thr Ala
    370             375

( 2 ) INFORMATION FOR SEQ ID NO: 9:

( i ) SEQUENCE CHARACTERISTICS:
        ( A ) LENGTH: 219 amino acid residues
        ( B ) TYPE: amino acid
        ( D ) TOPOLOGY: linear ( x i ) SEQUENCE DESCRIPTION: SEQ ID NO: 9:

Met Ala Leu Gly Arg Cys Ile Ala Glu Gly Trp Thr Leu Glu Arg Val
            5               10                  15

Ala Val Lys Gln Val Ser Trp Phe Leu Ile Tyr Ser Trp Val Cys Ser
            20              25              30

Gly Val Cys Arg Gly Val Ser Val Pro Glu Gln Gly Gly Gly Gly Gln
        35              40              45

Lys Ala Gly Ala Phe Thr Cys Leu Ser Asn Ser Ile Tyr Arg Ile Asp
    50              55              50

Cys His Trp Ser Ala Pro Glu Leu Gly Gln Glu Ser Arg Ala Trp Leu
65              70              75                          80

Leu Phe Thr Ser Asn Gln Val Thr Glu Ile Lys His Lys Cys Thr Phe
            85              90              95

Trp Asp Ser Met Cys Thr Leu Val Leu Pro Phe Glu Glu Val Phe Leu
            100             105             110

Pro Phe Asp Asn Phe Thr Ile Thr Leu His Arg Cys Ile Met Gly Gln
        115             120             125

Glu Gln Val Ser Leu Val Asp Ser Gln Tyr Leu Pro Arg Arg His Ile
    130             135             140

Lys Leu Asp Pro Pro Ser Asp Leu Gln Ser Asn Val Ser Ser Gly Arg
145             150             155             160

Cys Val Leu Thr Trp Gly Ile Asn Leu Ala Leu Glu Pro Leu Ile Thr
            165             170             175

Ser Leu Ser Tyr Glu Leu Ala Phe Lys Arg Gln Glu Glu Ala Trp Glu
            180             185             190

Ala Arg His Lys Lys Asp Arg Ile Val Gly Val Thr Trp Leu Ile Leu
        195             200             205

Glu Ala Val Glu Leu Asn Pro Glu Lys Arg Met
    210             215

( 2 ) INFORMATION FOR SEQ ID NO: 10:

( i ) SEQUENCE CHARACTERISTICS:
    ( A ) LENGTH: 522 amino acid residues
    ( B ) TYPE: amino acid
    ( D ) TOPOLOGY: linear ( x i ) SEQUENCE DESCRIPTION: SEQ ID NO: 10:

| Met | Gly | Leu | Gly | Arg | Cys | Ile | Trp | Glu | Gly | Trp | Thr | Leu | Glu | Ser | Glu |
|---|---|---|---|---|---|---|---|---|---|---|---|---|---|---|---|
| 1 | | | | 5 | | | | | 10 | | | | | 15 | |
| Ala | Leu | Arg | Arg | Asp | Met | Gly | Thr | Trp | Leu | Leu | Ala | Cys | Ile | Cys | Ile |
| | | | 20 | | | | | 25 | | | | 30 | | | |
| Cys | Thr | Cys | Val | Cys | Leu | Gly | Val | Ser | Val | Thr | Gly | Glu | Gly | Gln | Gly |
| | | 35 | | | | | 40 | | | | | 45 | | | |
| Pro | Arg | Ser | Arg | Thr | Phe | Thr | Cys | Leu | Thr | Asn | Asn | Ile | Leu | Arg | Ile |
| | 50 | | | | | 55 | | | | | 60 | | | | |
| Asp | Cys | His | Trp | Ser | Ala | Pro | Glu | Leu | Gly | Gln | Gly | Ser | Ser | Pro | Trp |
| 65 | | | | | 70 | | | | | 75 | | | | | 80 |
| Leu | Leu | Phe | Thr | Ser | Asn | Gln | Ala | Pro | Gly | Gly | Thr | His | Lys | Cys | Ile |
| | | | | 85 | | | | | 90 | | | | | 95 | |
| Leu | Arg | Gly | Ser | Glu | Cys | Thr | Val | Val | Leu | Pro | Pro | Glu | Ala | Val | Leu |
| | | | 100 | | | | | 105 | | | | | 110 | | |
| Val | Pro | Ser | Asp | Asn | Phe | Thr | Ile | Thr | Phe | His | His | Cys | Met | Ser | Gly |
| | | | 115 | | | | | 120 | | | | | 125 | | |
| Arg | Glu | Gln | Val | Ser | Leu | Val | Asp | Pro | Glu | Tyr | Leu | Pro | Arg | Arg | His |
| | 130 | | | | | 135 | | | | | 140 | | | | |
| Val | Lys | Leu | Asp | Pro | Pro | Ser | Asp | Leu | Gln | Ser | Asn | Ile | Ser | Ser | Gly |
| 145 | | | | | 150 | | | | | 155 | | | | | 160 |
| His | Cys | Ile | Leu | Thr | Trp | Ser | Ile | Ser | Pro | Ala | Leu | Glu | Pro | Met | Thr |
| | | | | 165 | | | | | 170 | | | | | 175 | |
| Thr | Leu | Leu | Ser | Tyr | Glu | Leu | Ala | Phe | Lys | Lys | Gln | Glu | Glu | Ala | Trp |
| | | | 180 | | | | | 185 | | | | | 190 | | |
| Glu | Gln | Ala | Gln | His | Arg | Asp | His | Ile | Val | Gly | Val | Thr | Trp | Leu | Ile |
| | | | 195 | | | | | 200 | | | | | 205 | | |
| Leu | Glu | Ala | Phe | Glu | Val | Asp | Pro | Gly | Phe | Ile | His | Glu | Ala | Arg | Leu |
| | 210 | | | | | 215 | | | | | 220 | | | | |
| Arg | Val | Gln | Met | Ala | Thr | Leu | Glu | Asp | Asp | Val | Val | Glu | Glu | Glu | Arg |
| 225 | | | | | 230 | | | | | 235 | | | | | 240 |
| Tyr | Thr | Gly | Gln | Trp | Ser | Glu | Trp | Ser | Gln | Pro | Val | Cys | Phe | Gln | Ala |
| | | | | 245 | | | | | 250 | | | | | 255 | |
| Pro | Gln | Arg | Gln | Gly | Pro | Leu | Ile | Pro | Pro | Trp | Gly | Trp | Pro | Gly | Asn |
| | | | 260 | | | | | 265 | | | | | 270 | | |
| Thr | Leu | Val | Ala | Val | Ser | Ile | Phe | Leu | Leu | Leu | Thr | Gly | Pro | Thr | Tyr |
| | | | 275 | | | | | 280 | | | | | 285 | | |
| Leu | Leu | Phe | Lys | Leu | Ser | Pro | Arg | Val | Lys | Arg | Ile | Phe | Tyr | Gln | Asn |
| | | 290 | | | | | 295 | | | | | 300 | | | |
| Val | Pro | Ser | Pro | Ala | Met | Phe | Phe | Gln | Pro | Leu | Tyr | Ser | Val | His | Asn |
| 305 | | | | | 310 | | | | | 315 | | | | | 320 |
| Gly | Asn | Phe | Gln | Thr | Trp | Met | Gly | Ala | His | Arg | Ala | Gly | Val | Leu | Leu |
| | | | | 325 | | | | | 330 | | | | | 335 | |
| Ser | Gln | Asp | Cys | Ala | Gly | Thr | Pro | Gln | Gly | Ala | Leu | Glu | Pro | Cys | Val |
| | | | 340 | | | | | 345 | | | | | 350 | | |
| Gln | Glu | Ala | Thr | Ala | Leu | Leu | Thr | Cys | Gly | Pro | Ala | Arg | Pro | Trp | Lys |
| | | | 355 | | | | | 360 | | | | | 365 | | |
| Ser | Val | Ala | Leu | Glu | Glu | Glu | Gln | Glu | Gly | Pro | Gly | Thr | Arg | Leu | Pro |
| | 370 | | | | | 375 | | | | | 380 | | | | |

|       |       |       |       |       |       |       |       |       |       |       |       |       |       |       |
|-------|-------|-------|-------|-------|-------|-------|-------|-------|-------|-------|-------|-------|-------|-------|
| Gly   | Asn   | Leu   | Ser   | Ser   | Glu   | Asp   | Val   | Leu   | Pro   | Ala   | Gly   | Cys   | Thr   | Glu   | Trp   |
| 385   |       |       |       |       | 390   |       |       |       |       | 395   |       |       |       |       | 400   |

Arg Val Gln Thr Leu Ala Tyr Leu Pro Gln Glu Asp Trp Ala Pro Thr
                405                 410             415

Ser Leu Thr Arg Pro Ala Pro Pro Asp Ser Glu Gly Ser Arg Ser Ser
            420             425             430

Ser Ser Ser Ser Ser Ser Ser Asn Asn Asn Asn Tyr Cys Ala Leu Gly
        435             440                 445

Cys Tyr Gly Gly Trp His Leu Ser Ala Leu Pro Gly Asn Thr Gln Ser
    450             455             460

Ser Gly Pro Ile Pro Ala Leu Ala Cys Gly Leu Ser Cys Asp His Gln
465             470             475                     480

Gly Leu Glu Thr Gln Gln Gly Val Ala Trp Val Leu Ala Gly His Cys
            485             490                     495

Gln Arg Pro Gly Leu His Glu Asp Leu Gln Gly Met Leu Leu Pro Ser
            500             505             510

Val Leu Ser Lys Ala Arg Ser Trp Thr Phe
            515             520          .

(2) INFORMATION FOR SEQ ID NO: 11:

(i) SEQUENCE CHARACTERISTICS:
        (A) LENGTH: 307 amino acid residues
        (B) TYPE: amino acid
        (D) TOPOLOGY: linear (xi) SEQUENCE DESCRIPTION: SEQ ID NO: 11:

Met Gly Leu Gly Arg Cys Ile Trp Glu Gly Trp Thr Leu Glu Ser Glu
                5               10                  15

Ala Leu Arg Arg Asp Met Gly Thr Trp Leu Leu Ala Cys Ile Cys Ile
            20              25                  30

Cys Thr Cys Val Cys Leu Gly Val Ser Val Thr Gly Glu Gly Gln Gly
        35              40              45

Pro Arg Ser Arg Thr Phe Thr Cys Leu Thr Asn Asn Ile Leu Arg Ile
    50              55              60

Asp Cys His Trp Ser Ala Pro Glu Leu Gly Gln Gly Ser Ser Pro Trp
65              70              75                      80

Leu Leu Phe Thr Ser Asn Gln Ala Pro Gly Gly Thr His Lys Cys Ile
            85              90                  95

Leu Arg Gly Ser Glu Cys Thr Val Val Leu Pro Pro Glu Ala Val Leu
            100             105             110

Val Pro Ser Asp Asn Phe Thr Ile Thr Phe His His Cys Met Ser Gly
    115             120             125

Arg Glu Gln Val Ser Leu Val Asp Pro Glu Tyr Leu Pro Arg Arg His
    130             135             140

Val Lys Leu Asp Pro Pro Ser Asp Leu Gln Ser Asn Ile Ser Ser Gly
145             150             155                     160

His Cys Ile Leu Thr Trp Ser Ile Ser Pro Ala Leu Glu Pro Met Thr
            165             170             175

Thr Leu Leu Ser Tyr Glu Leu Ala Phe Lys Lys Gln Glu Glu Ala Trp
            180             185             190

Glu Gln Ala Gln His Arg Asp His Ile Val Gly Val Thr Trp Leu Ile
        195             200             205

Leu Glu Ala Phe Glu Val Asp Pro Gly Phe Ile His Glu Ala Arg Leu
    210             215             220

Arg Val Gln Met Ala Thr Leu Glu Asp Asp Val Val Glu Glu Glu Arg

```
                225                       230                       235                       240
Tyr   Thr   Gly   Gln   Trp   Ser   Glu   Trp   Ser   Gln   Pro   Val   Cys   Phe   Gln   Ala
                        245                       250                       255
Pro   Gln   Arg   Gln   Gly   Pro   Leu   Ile   Pro   Pro   Trp   Gly   Trp   Pro   Gly   Asn
                  260                       265                       270
Thr   Leu   Val   Ala   Val   Ser   Ile   Phe   Leu   Leu   Leu   Thr   Gly   Pro   Thr   Tyr
            275                       280                       285
Leu   Leu   Phe   Lys   Leu   Ser   Pro   Arg   Leu   Gly   Trp   Gly   Pro   Thr   Gly   Pro
      290                       295                       300
Val   Cys   Cys
305
```

( 2 ) INFORMATION FOR SEQ ID NO: 12:

( i ) SEQUENCE CHARACTERISTICS:
        ( A ) LENGTH: 536 amino acid residues
        ( B ) TYPE: amino acid
        ( D ) TOPOLOGY: linear ( x i ) SEQUENCE DESCRIPTION: SEQ ID NO: 12:

```
Met   Leu   Trp   Leu   Val   Val   Pro   Gly   Cys   Thr   Leu   His   Ser   Arg   Lys   Gly
                        5                         10                        15
Ala   Leu   Ser   Gln   Ser   Leu   Ala   Gly   Trp   Thr   Leu   Glu   Ser   Glu   Ala   Leu
                  20                        25                        30
Arg   Arg   Asp   Met   Gly   Thr   Trp   Leu   Leu   Ala   Cys   Ile   Cys   Ile   Cys   Thr
            35                        40                        45
Cys   Val   Cys   Leu   Gly   Val   Ser   Val   Thr   Gly   Glu   Gly   Gln   Gly   Pro   Arg
      50                        55                        60
Ser   Arg   Thr   Phe   Thr   Cys   Leu   Thr   Asn   Asn   Ile   Leu   Arg   Ile   Asp   Cys
65                        70                        75                        80
His   Trp   Ser   Ala   Pro   Glu   Leu   Gly   Gln   Gly   Ser   Ser   Pro   Trp   Leu   Leu
                        85                        90                        95
Phe   Thr   Ser   Asn   Gln   Ala   Pro   Gly   Gly   Thr   His   Lys   Cys   Ile   Leu   Arg
                  100                       105                       110
Gly   Ser   Glu   Cys   Thr   Val   Val   Leu   Pro   Pro   Glu   Ala   Val   Leu   Val   Pro
            115                       120                       125
Ser   Asp   Asn   Phe   Thr   Ile   Thr   Phe   His   His   Cys   Met   Ser   Gly   Arg   Glu
      130                       135                       140
Gln   Val   Ser   Leu   Val   Asp   Pro   Glu   Tyr   Leu   Pro   Arg   Arg   His   Val   Lys
145                       150                       155                       160
Leu   Asp   Pro   Pro   Ser   Asp   Leu   Gln   Ser   Asn   Ile   Ser   Ser   Gly   His   Cys
                        165                       170                       175
Ile   Leu   Thr   Trp   Ser   Ile   Ser   Pro   Ala   Leu   Glu   Pro   Met   Thr   Thr   Leu
                  180                       185                       190
Leu   Ser   Tyr   Glu   Leu   Ala   Phe   Lys   Lys   Gln   Glu   Glu   Ala   Trp   Glu   Gln
            195                       200                       205
Ala   Gln   His   Arg   Asp   His   Ile   Val   Glu   Val   Thr   Trp   Leu   Ile   Leu   Glu
      210                       215                       220
Ala   Phe   Glu   Leu   Gln   Pro   Gly   Phe   Ile   His   Glu   Ala   Arg   Leu   Arg   Val
225                       230                       235                       240
Gln   Met   Ala   Thr   Leu   Gly   Asp   Asp   Val   Val   Glu   Glu   Glu   Arg   Tyr   Thr
                        245                       250                       255
Gly   Gln   Trp   Ser   Glu   Trp   Ser   Gln   Pro   Val   Cys   Phe   Gln   Arg   Pro   Gln
                  260                       265                       270
Arg   Gln   Gly   Pro   Leu   Ile   Pro   Pro   Trp   Gly   Trp   Pro   Gly   Asn   Thr   Leu
            275                       280                       285
```

```
Val  Ala  Val  Ser  Ile  Phe  Leu  Leu  Thr  Gly  Pro  Thr  Tyr  Leu  Leu
     290            295                      300

Phe  Lys  Leu  Ser  Pro  Arg  Val  Lys  Arg  Ile  Phe  Tyr  Gln  Asn  Val  Pro
305                 310                      315                           320

Ser  Pro  Ala  Met  Phe  Phe  Gln  Pro  Leu  Tyr  Ser  Val  His  Asn  Gly  Asn
                    325                      330                           335

Phe  Gln  Thr  Trp  Met  Gly  Ala  His  Arg  Ala  Gly  Val  Leu  Leu  Ser  Gln
               340                      345                           350

Asp  Cys  Ala  Gly  Thr  Pro  Gln  Gly  Ala  Leu  Gly  Pro  Cys  Val  Gln  Glu
          355                      360                      365

Ala  Thr  Ala  Leu  Leu  Thr  Cys  Gly  Pro  Ala  Arg  Pro  Trp  Lys  Ser  Val
     370                      375                      380

Ala  Leu  Gly  Glu  Glu  Gln  Glu  Gly  Pro  Gly  Thr  Arg  Leu  Pro  Gly  Asn
385                      390                      395                      400

Leu  Ser  Ser  Glu  Asp  Val  Leu  Pro  Ala  Gly  Cys  Thr  Glu  Trp  Arg  Val
               405                      410                           415

Gln  Thr  Leu  Ala  Tyr  Leu  Pro  Gln  Glu  Asp  Trp  Ala  Pro  Thr  Ser  Leu
               420                 425                      430

Thr  Arg  Pro  Ala  Pro  Pro  Asp  Ser  Glu  Gly  Ser  Arg  Ser  Ser  Ser  Ser
          435                 440                      445

Ser  Ser  Ser  Ser  Ser  Asn  Asn  Asn  Asn  Tyr  Cys  Ala  Leu  Gly  Cys  Tyr
     450                 455                      460

Gly  Gly  Trp  His  Leu  Ser  Ala  Leu  Pro  Gly  Asn  Thr  Gln  Ser  Ser  Gly
465                      470                 475                           480

Pro  Ile  Pro  Ala  Leu  Ala  Cys  Gly  Leu  Ser  Cys  Asp  His  Gln  Gly  Leu
               485                      490                           495

Glu  Thr  Gln  Gln  Gly  Val  Ala  Trp  Val  Leu  Ala  Gly  His  Cys  Gln  Arg
               500                 505                      510

Pro  Gly  Leu  His  Glu  Asp  Leu  Gln  Gly  Met  Leu  Leu  Pro  Ser  Val  Leu
          515                 520                      525

Ser  Lys  Ala  Arg  Ser  Trp  Thr  Phe
     530                 535
```

NUCLEIC ACID SEQUENCES CODING FOR OR COMPLEMENTARY TO NUCLEIC ACID SEQUENCES CODING FOR INTERLEUKIN 9 RECEPTOR

This application is a continuation of application Ser. No. 07/847,347, filed Mar. 9, 1992, now abandoned.

FIELD OF THE INVENTION

This invention relates to the reception of the cytokine known as interleukin 9 by cells, via its receptor. More particularly, it relates to the isolation of nucleic acid sequences which code for interleukin 9 receptor molecules ("IL-9R" hereafter). These sequences can be used, e.g. as a source for IL-9 receptor, and as probes for cells which respond to the cytokine. The complementary sequences can be used to inhibit expression as well as to probe for the coding sequences.

BACKGROUND AND PRIOR ART

The last decade has seen knowledge of the immune system and its regulation expand tremendously. One area of particular interest has been that of research on the proteins and glycoproteins which regulate the immune system. Perhaps the best known of these molecules, which are generically referred to as "growth factors", "cytokines", "leukotrines", "lymphokines", etc., is interleukin-2 ("IL-2"). See, e.g., U.S. Pat. No. 4,778,879 to Mertelsmann et al.; U.S. Pat. No. 4,490,289, to Stern; U.S. Pat. No. 4,518,584, to Mark et al.; and U.S. Pat. No. 4,851,512 to Miyaji et al. Additional patents have issued which relate to interleukin 1—("IL-1"), such as U.S. Pat. No. 4,808,611, to Cosman. The disclosure of all of these patents are incorporated by reference herein.

In order for molecules such as IL-2 and IL-1 to exert their effect on cells, it is now pretty much accepted that these must interact with molecules, located on cell membranes, referred to as receptors. Patents which exemplify disclosures of interleukin receptors include Honjo et al., U.S. Pat. No. 4,816,565; and Urdal et al., U.S. Pat. No. 4,578,335, the disclosures of which are incorporated by reference. Recently, Fanslow, et al., Science 248: 739–41 (May 11, 1990) presented data showing that the effect of IL-1 in vivo could be regulated via the administration of a soluble form of its receptor. The last paragraph of the Fanslow paper, the disclosure of which is incorporated by reference, describes the types of therapeutic efficacy administration of soluble IL-1 receptor ("IL-1R") is expected to have.

The lymphokine IL-9, previously referred to as "P40", is a T-cell derived molecule which was originally identified as a factor which sustained permanent antigen independent growth of T4 cell lines. See, e.g., Uyttenhove, et al., Proc. Natl. Acad. Sci. 85: 6934 (1988), and Van Snick et al., J. Exp. Med. 169: 363 (1989), the disclosures of which are incorporated by reference, as is that of Simpson et al., Eur. J. Biochem. 183: 715 (1989).

The activity of IL-9 was at first observed to act on restricted T4 cell lines, failing to show activity on CTLs or freshly isolated T cells. See, e.g., Uyttenhove et al., supra, and Schmitt et al., Eur. J. Immunol. 19: 2167 (1989). This range of activity was expanded when experiments showed that IL-9 and the molecule referred to as T cell growth Factor III ("TCGF III") are identical. IL-9 enhances the proliferative effect of bone marrow derived mast cells to "IL-3", as is described by Hültner et al., Eur. J. Immunol. 20: 1413–1416 (1990) and in U.S. Pat. No. 5,164,317 the disclosures of both being incorporated by reference herein. It was also found that the human form of IL-9 stimulates proliferation of megakaryoblastic leukemia. See Yang et al., Blood 74: 1880 (1989). Recent work on IL9 has shown that it also supports erythroid colony formation (Donahue et al., Blood 75(12): 2271–2275 (Jun. 15, 1990)); promotes the proliferation of myeloid erythroid burst formation (Williams et al., Blood 76: 306–311 (Sep. 1, 1990)); and supports clonal maturation of BFU.E's of adult and fetal origin (Holbrook et al., Blood 77(10): 2129–2134 (May 15, 1991)). Expression of IL9 has also been implicated in Hodgkin's disease and large cell anaplastic lymphoma (Merz et al., Blood 78(8): 1311–1317 (Sep. 1, 1990)).

The art teaches the cloning of receptors for various members of the interleukin family. Moseley et al. Cell 59: 335–348 (1989), teach the isolation of cDNA coding for IL-4 receptors, and analysis of both genomic DNA and RNA for these molecules. To do this, Moseley et al. worked with cells exhibiting up to 1 million receptor molecules per cell, and an N-terminal amino acid sequence for IL-4 receptor. Holmes et al., Science 253: 1278–1280 (1991), and Murphy et al., Science 253: 1280–1282 (1991) discuss cDNA for the IL-8 receptor. Murphy et al. proceeded via hybridization studies, using an oligonucleotide probe based upon rabbit IL-8R amino acid sequences to isolate the human counterpart. Holmes et al. used human neutrophil cDNA libraries followed by transfection in COS cells.

Gillis, "T-cell Derived Lymphokines" in Paul, ed., Fundamental Immunology, Second Edition (New York, 1989), at pages 632 et seq. gives an overview of interleukin receptors. This reference describes cDNA for the IL1 receptor, the IL2 receptor and the IL-6 receptor.

These studies indicate that several factors are important in attempting to identify and isolate a nucleic acid sequence coding for an interleukin receptor. Ideally, one has both the amino acid sequence for the receptor and a cell type with a high degree of expression of the receptor molecule.

In the case of the interleukin 9 receptor, while Druez et al., J. Immunol. 145: 2494–2499 (1990) have identified and characterized the receptor as a glycoprotein with a molecular weight of 64 kilodaltons the protein portion of which has a molecular weight of 54 kilodalton as determined by SDS-PAGE, an amino acid sequence of the molecule is not yet available. In addition, very few cell types are known which express IL9-R (Druez, supra), and those that do, express it at very low levels. Thus, it is surprising that it is now possible to identify and to isolate nucleic acid sequences which code for the interleukin 9 receptor. This is the key feature of the invention described herein, as will be seen from the disclosure which follows.

BRIEF DESCRIPTION OF THE FIGURES

FIG. 2 aligns deduced human SEQ ID NO: 10 and murine SEQ ID NO: 7 IL-9R amino acid sequences.

DETAILED DESCRIPTION OF THE PREFERRED EMBODIMENTS

EXAMPLE 1

Figure 1:
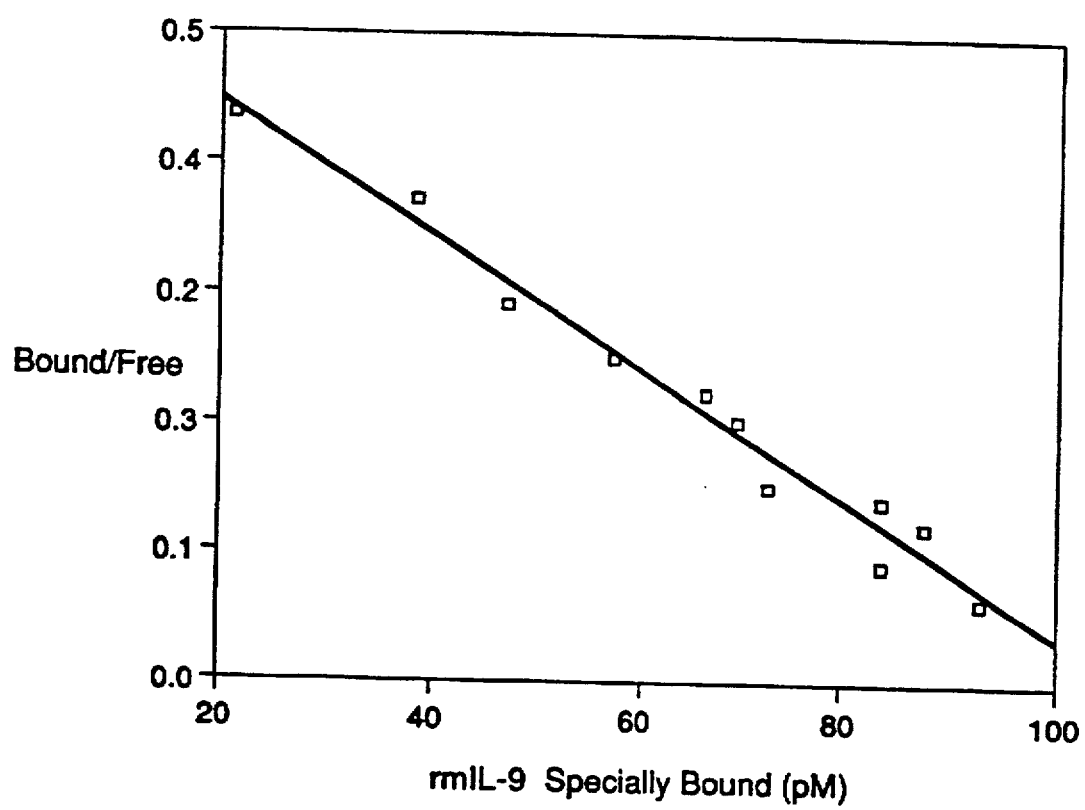
FIG. 1 presents Scatchard analysis of expression of murine IL9 receptor following transfection of COS cells.

The murine T cell clone, TS1, described by, e.g., Uyttenhove et al., Proc. Natl. Acad. Sci. 85: 6934–6938 (1988) the disclosure of which is incorporated by reference, expresses approximately 200 high affinity binding sites for IL-9, i.e., it expresses the IL-9 receptor molecule. See Druez et al., J. Immunol. 145: 2494–2499 (1990). This cell line, while presenting few receptor molecules, does show the highest density of IL9R of all cells tested, and thus was selected as a source of mRNA for constructing a cDNA library.

Poly(A)+ mRNA was extracted from TS1 cells, and was then converted to double stranded cDNA using random hexanucleotide primers, following Grubler et al. Gene 25: 263–269 (1983), the disclosure of which is incorporated by reference.

Following this, EcoRI adaptors were attached, and any cDNA larger than 1.5 kilobases was isolated by fractionation on a 5–20% potassium acetate gradient, following Aruffo et al., Proc. Natl. Acad. Sci. 84: 8573–8577 (1987).

The size selected cDNA was then inserted into the ECORI site of expression vector pCDSRα taught by Takebe et al., Mol. Cell Biol. 8: 466–472 (1988). This was then transfected into *E. coli* strain XL1-blue using standard transformation procedures. (Maniatis). In order to screen for clones expressing IL-9R, plasmid DNA from the cDNA library was tested for the ability to express IL-9 binding activity by expression in COS cells. Basically, the cDNA library was subfractionated into 100 pools of about 500 clones each, and the DNA was transfected using the DEAE-dextran-chloroquine method of Aruffo et al., supra, into $1.5 \times 10^5$ COS cells, seeded on glass microscope slides. Cells were allowed to grow for 2–3 days, and were then tested for expression of IL-9R with $^{125}$I labelled, purified recombinant murine IL9. This labeled material was prepared following Bolton et al., Biochem. J. 133: 529–539 (1973). The cells were incubated for three hours at 20° C. with 0.2 nM of this material, washed briefly, fixed, and then dipped into liquid photographic emulsion. The slides were exposed for 10 days, then developed and examined microscopically for autoradiographic grains.

This screening resulted in two positive pools out of 100. One positive pool showed a single positive cell, and the second one showed 33 positive cells. This latter pool was selected for further testing, and was divided, first into 100 pools of 15 clones each, after which a single positive pool was selected, and divided into 100 single clones.

EXAMPLE 2

Following the separating and replating described at the end of example 1, supra, the screening methodology described therein was employed on the replated cells, and led to identification of a clone containing a plasmid referred to as p9RA1. Since the "source" plasmid pCDSRα was known and characterized, it was possible using standard methodologies to identify the insert as 1900 base pairs in length.

EXAMPLE 3

Using the p9RA1 1900 base pair segment as a probe, additional screening was carried out to identify additional murine IL9R receptor cDNA clones. The methodology followed was that of Maniatis et al., Molecular Cloning, a Laboratory Manual (Cold Spring Harbor Laboratory, New York, 1982), where the p9RA1 probe was hybridized to two further cDNA libraries which were generated in the BstXI site of vector pCDM8 (Aruffo et al. supra), using oligo T or random primers, followed by high stringency washes.

This methodology resulted in the identification of six additional clones. Two of these were oligo-dT primed cDNAs, and are referred to as p9RB1, and p9RB3, and four random primed clones p9RC2, p9RC3, p9RC4 and p9CR9. The sizes of these clones are as follows:

| | |
|---|---|
| p9RB1 | 1600 bp |
| p9RB3 | 900 bp |
| p9RC2 | 2000 bp |
| p9RC3 | 1000 bp |
| p9RC4 | 3000 bp |
| p9RC9 | 2100 bp |

EXAMPLE 4

In order to make sure that clone p9RA1 and all subsequent clones did in fact express IL9R. Scatchard analysis was carried out on transfected COS cells, following Goodwin et al., Cell 60: 941–951 (1990). This analysis, shown in FIG. 1, identified a single class of binding sites with a Kd of 194 pM, when p9RA1 was used. This is slightly higher than the dissociation constant measured on TS1 cells previously, i.e., 67 pM.

When the largest cDNA was tested (i.e., the C4 clone), high affinity binding sites for IL9 were also identified, with a Kd of 126 pM.

EXAMPLE 5

Figure 2:
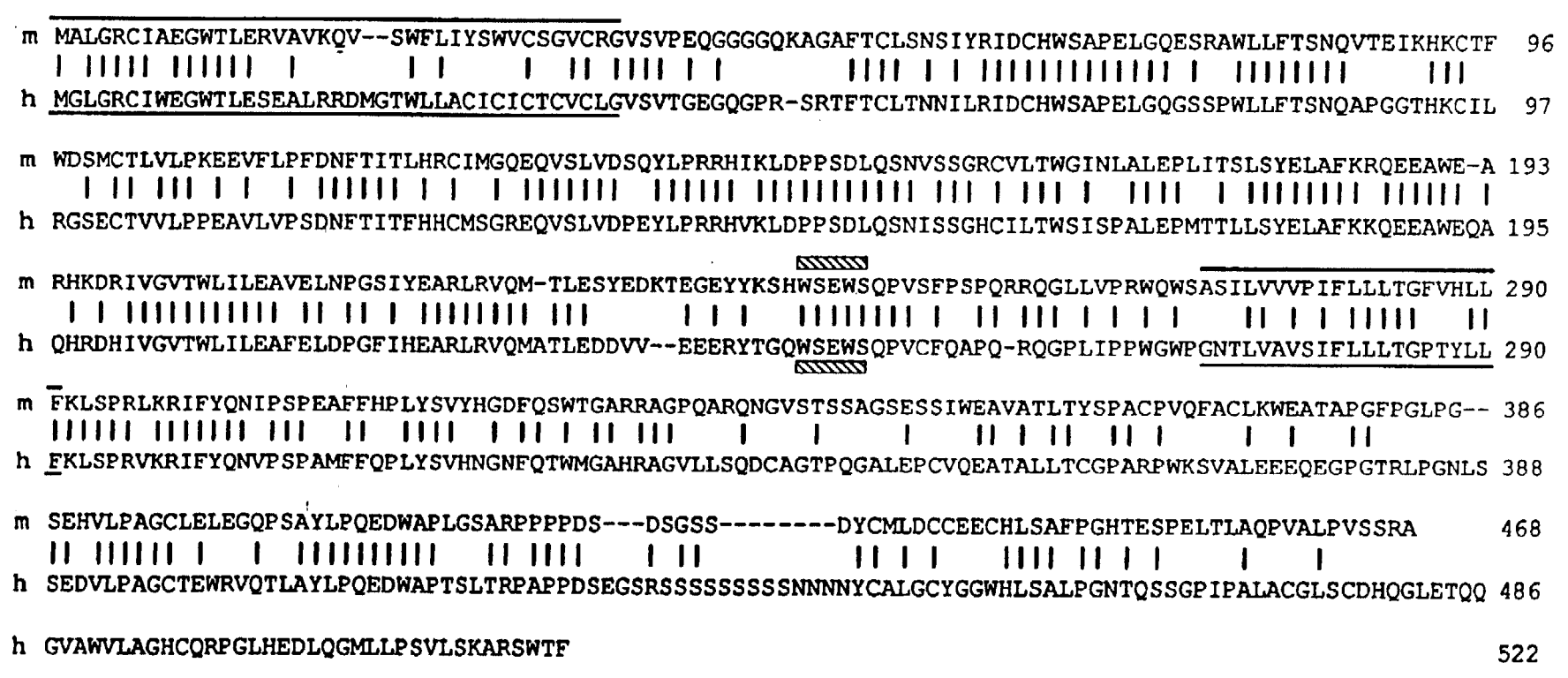

Following the isolation of murine clones, tests were also carried out to isolate analogous human material. To do this, a megakaryoblast cell line, i.e., Mo7E was used as a source of mRNA to make double stranded cDNA as per example 1. The plasmid pRC/RSV was used to receive the cDNA. This cDNA library was screened, using p9RA1 as a probe, and hybridization was carried out using the same conditions described supra, except washes were carried out at low stringency (2×SSC, 0.1% SDS, 55° C.). Six clones were isolated, i.e., ph9RA2, 3, 4, 5, 6 and 9, and sequenced. The clone ph9RA3 contained a 1566 base pair open reading frame, which showed 66% identity with murine p9RC4. The deduced murine (m) SEQ ID NO:7 and human (h) SEQ ID NO:10 protein sequences are shown in FIG. 2, with a 53% identity over 522 amino acids.

EXAMPLE 6

In order to test whether clone ph9RA3 actually did code for a human IL9 receptor, the clone was transfected into murine cell line TS1, using double pulse electroporation. In brief, $5\times10^6$ TS1 cells were resuspended at 37° C. in 0.8 ml of Dulbecco's modified Eagle's medium, supplemented with 10% fetal bovine serum, 50 mM 2-mercaptoethanol, 0.55 mM L-arginine, 0.24 mM L-asparagine, and 1.25 mM L-glutamine. Plasmid DNA (50 ug) was added to the cells in 0.4 cm cuvettes just before electroporation. After a double electric pulse (750 V, 7452 Ω, 40 μF and 100 V, 74 Ω, 2100 μF), cells were immediately diluted in fresh medium supplemented with murine IL9. After 24 hours, cells were washed and cultured in the presence of G418, and mouse IL9. These conditions resulted in a frequency of transfection of approximately 1/10,000. Following selection with G418, transfected cells were maintained in human IL9, and a TS1 proliferation assay was performed using the methodology of Uyttenhove et al., Proc. Natl., Acad. Sci. USA 85: 6934–6938 (1988). If the cDNA expresses hIL9R, then cells should proliferate, while those which do not contain it should not.

Figure 3A:
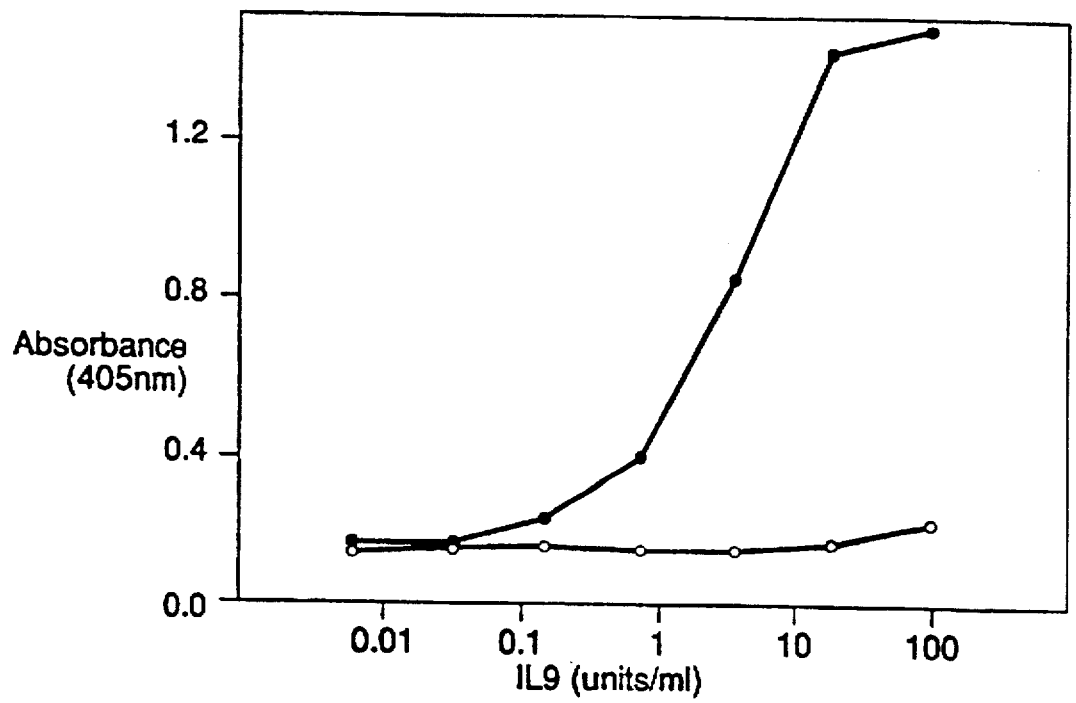
FIG. 3 compares the response of TS1 cells, both before and after transfection with DNA coding for human IL-9R.
Figure 3B:
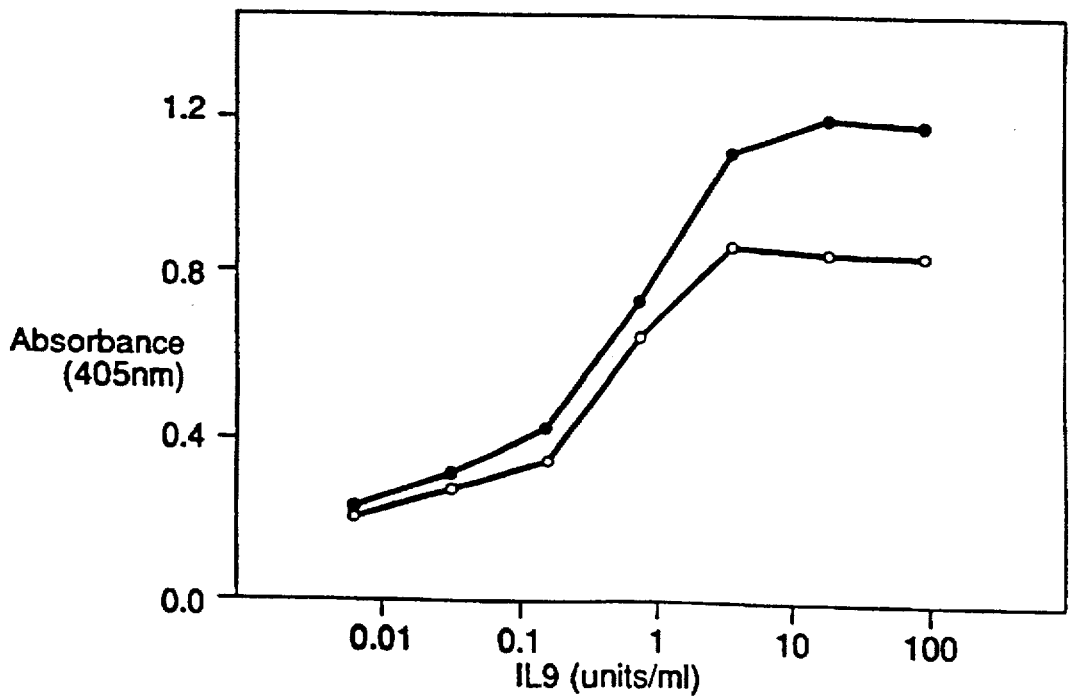

FIG. 3 shows that original TS1 cells, unresponsive to 100 units/ml of human IL9, became responsive and proliferated after transfection with the human IL9R cDNA.

EXAMPLE 7

The sequence of clone p9RC4, presented as SEQ ID NO: 1, shows an open reading frame coding a 468 amino acid protein. The deduced amino acid sequence predicts two hydrophobic regions, one of which spans amino acids 15-40, and probably represents a signal peptide. The probability weight matrix of von Heyne, Nucl. Acids Res. 14: 4683-4690 (1986) predicts a cleavage site for the signal peptide between positions 37 and 39. The second hydrophobic domain spans amino acids 271-291. This is presumed to constitute the transmembrane domain.

The putative extracellular domain contains 233 amino acids, including 6 cysteine residues and two potential N-linked glycosylation sites at positions 116 and 155. A "WSEWS" motif, typical of the hematopoietin receptor superfamily described by Idzerda et al., J. Exp. Med. 171: 861-873 (1990), is found at positions 244-248.

The cytoplasmic portion of the molecule is characterized by a high percentage of serine (13%), and proline (12.4%), as well as three potential protein kinase C phosphorylation sites at positions 294, 416 and 465.

Comparison of the various clones indicates that p9RA1 and p9RB3 contain an additional glutamine between position 192 and 193 as compared to p9RC4, but without a frameshift. This residue lies in the extracellular domain, but as example 4, supra shows, it does not appear to affect the affinity for ligand. There is a 22 nucleotide deletion at this position in p9RC2. These features, and a potential intronic sequence in p9RC9, suggest alternate splicing events.

The analysis of p9RB3 implies the existence of a soluble form of IL9R. The cDNA for this clone contains a large part of extracellular domain, but lacks nucleotides 651-1719, which code the end of the N-terminal domain, the transmembrane and the cytoplasmic domain.

Clone p9RA1 is different from all other clones in that there is a stop codon after alanine (378), which is followed by a 736 base pair sequence unrelated to any other cDNA's sequenced.

The sequences for the murine cDNA described in this example is provided as follows:

p9RC4 (SEQ ID NO: 1)
p9RA1 (SEQ ID NO: 2)
p9RB3 (SEQ ID NO: 3).

The deduced amino acid sequences for these cDNAs are presented as SEQ ID NOS: 7, 8 and 9, respectively.

EXAMPLE 8

The cDNA for human IL9-R was also analyzed. As indicated supra, clone ph9RA3 showed 66% identity with murine p9RC4 and 53% homology on the amino acid sequence level. A putative cleavage site is positioned between amino acids 39 and 40. This site is conserved between species, as is the transmembrane domain, the two potential N-glycosylation sites, and the consensus sequence for the hematopoietic superfamily, all of which are described in Example 7.

The cytoplasmic portion of the protein seemed less conserved, and was much larger (231 amino acids) than the murine counterpart (177 residues). Due to a stretch of 9 consecutive serines in positions 431-439, there is a high percentage of serine in the molecule (11.2%).

Clones ph9RA2, 4, 6 and 9 confirmed the sequence derived from ph9RA3. The clone ph9RA5, however, has an 85 nucleotide deletion in positions 1063-1147, suggesting a truncated protein. The putative truncated protein would be 307 amino acids long, and contain the complete extracellular and transmembrane regions of IL9-R, 5 amino acids of the cytoplasmic domain, and 11 unrelated residues.

The clone referred to as pH9RA6 contains a short intervening sequence at the beginning of the DNA, which leads into a stop codon, in frame with the normal initiative codon. It also creates a new ATG triplet in frame with the downstream portion of the coding sequence. In the IL9R molecule, this yields a transcript with a unique N-terminal sequence, the rest of the sequence being identical to pH9RA3. Comparison of pH9RA6 and pH9RA3 shows that, after the initial methionine common to both clones, pH9RA6 contains an insert of 22 amino acids. These are followed by the sequence "Gly Trp Thr Lve Glo Ser Glu . . . " which is nucleotides 10-16 SEQ ID NO: 10.

The nucleic acid sequences for ph9RA3, ph9RA5 and pH9RA6 are presented as SEQ ID NO: 4, SEQ ID NO: 5 and SEQ ID NO: 6, respectively. The deduced amino acid sequences encoded by these are presented as SEQ ID NOS: 10, 11 and 12, respectively.

The foregoing teaches the isolation of a nucleic acid sequence which codes for the interleukin-9 receptor. The homology found therebetween (53%, with up to 67% in the extracellular region) suggests that nucleic acid sequences coding for IL9-R from other species could also be identified.

The preceding data deal with cDNA, but it will be seen that the sequences of the cDNA put one in possession of mRNA, as the latter can be derived from the former based on well known rules regarding construction of the sequences. Given the cDNA information, it is presumed that one could also secure the genomic analogs of the cDNAs.

The information provided herein also teaches construction of vectors, such as plasmids, which contain the nucleic acid sequences of interest, i.e., those coding for mammalian IL9R. Such vectors may contain components in addition to the coding sequence, such as promoters operably linked to the coding sequence, "markers", such as genes for antibiotic resistance or selection, including the thymidine kinase or "TK" gene, as well as others which will be known to the skilled artisan. The nucleic acid sequences and vectors may be used—as has been shown—to transfect various cell types, such as "COS", "CHO", Spodoptera frugiperda or other insect cell lines. The sequences, either alone or in appropriate vectors, can be used to transfect a panoply of prokaryotic and eukaryotic cells.

The isolation of nucleic acid sequences coding for the IL9 receptor makes it possible for investigators to carry out several lines of investigation which were not possible or much more difficult without these. For example, as pointed out supra, even on these cells which express it best, expression of IL-9R is low. Isolation of the gene makes it possible to transfect recipient cells, followed by overexpression, amplification, etc. This leads to sufficient expression on cell surfaces to permit immunization with these cells, and generation of an immunogenic response to IL-9R, including the production of antibodies. Isolation of the antibody producing cells, followed by standard techniques of hybridoma biology leads to production of IL-9R specific monoclonal antibodies.

The antibodies produced, be they polyclonal or monoclonal, can then be used in therapeutic methods to block IL-9 from binding to IL-9R molecules. As binding of IL-9 to cell surfaces is implicated in several pathological conditions, this is an important therapeutic goal.

In addition IL-9R specific antibodies can be used for both qualitative and quantitative measurement of IL-9R expression on cells, following known immunoassay protocols.

The examples supra show the existence of a soluble form of IL-9R. As with other soluble interleukin receptor molecules (see Fanslow et al., supra), this molecule can be used to prevent the binding of IL-9 to cell bound receptor, and thus interfere with the affect of IL-9 on a cell type, subpopulation, etc. As such, soluble IL-9R may be said to be an antagonist for IL-9.

Recent work has shown that the soluble form of one interleukin receptor, i.e., IL-6R, functions as an agonist. See Taga et al., Cell 58: 573–591 (Aug. 11, 1989). The soluble form of IL-9R might function in a similar manner. In addition the IL-9R molecule, either the soluble form or a solubilized form of the molecule may be used as an immunogen for generation of IL-9R specific antibodies. Either the entire receptor molecule, or an immunogenic portion thereof, can be used in an appropriate animal, such as a mouse, rabbit or guinea pig, to generate an immune response which includes antibody formation. The antibodies can then be purified using standard techniques. Alternatively, antibody producing B cells can be isolated and utilized in any of the standard methods for producing hybridomas, so as to lead to the generation of IL-9R specific monoclonal antibodies.

An assay is described supra, in Example 6, in which IL-9R cDNA expression is assayed by measuring the responsiveness of a transfected cell line to IL9. This assay methodology provides a means for screening for various agonists and antagonists. In brief, a transfected cell sample containing a sequence coding for IL9R is contacted with a compound of interest. If the compound is an agonist, it will bind to the IL-9R molecule on the cell surface, and lead to the series of events usually associated with IL-9/IL-9R binding. To the same end, an antagonist can be assayed by combining the compound of interest with IL-9 and the cell sample to determine whether the IL-9 has diminished impact, or no impact. The assay for agonist/antagonist may be viewed as part of a broader invention wherein one may assay for molecules which compete for binding to IL-9R.

In addition to the coding sequences discussed herein, the invention also embraces sequences complementary to the coding sequences. These complements, which can be derived from the coding sequences themselves, may be used, e.g., as probes or as "anti-sense" inhibitors to prevent expression of the IL9R coding sequences. Other aspects of the invention will be clear to the skilled artisan, and do not require elaboration here.

The terms and expressions which have been employed are used as terms of description and not of limitation, and there is no intention in the use of such terms and expressions of excluding any equivalents of the features shown and described or portions thereof, it being recognized that various modifications are possible within the scope of the invention.

We claim:

1. Isolated nucleic acid molecule the complementary sequence of which hybridizes under low stringency conditions to a nucleic acid molecule having a nucleotide sequence selected from the group consisting of SEQ ID NO: 1, SEQ ID NO: 2, SEQ ID NO: 3, SEQ ID NO: 4, SEQ ID NO: 5 and SEQ ID NO: 6.

2. The isolated nucleic acid molecule of claim 1, wherein said nucleic acid molecule is cDNA.

3. Microorganism transfected with the nucleic acid molecule of claim 1.

4. The microorganism of claim 3, wherein said microorganism is *Escherichia coli*.

5. Cell line transfected with the nucleic acid molecule of claim 1.

6. The cell line of claim 5, wherein said cell line is a eukaryotic cell line.

7. The cell line of claim 6, wherein said eukaryotic cell line is a CHO cell line or a COS cell line.

8. The cell line of claim 6, wherein said eukaryotic cell line is a yeast cell line.

9. The cell line of claim 6, wherein said cell line is an insect cell line.

10. The cell line of claim 9, wherein said cell line is *Spodoptera frugiperda*.

11. The isolated nucleic acid molecule of claim 1, having the nucleotide sequence set forth in SEQ ID NO: 1, SEQ ID NO: 2, SEQ ID NO: 3, SEQ ID NO: 4, SEQ ID NO: 5 or SEQ ID NO: 6.

12. The isolated nucleic acid molecule of claim 1, which encodes for a protein having an amino acid sequence selected from the group consisting of SEQ ID NO: 7, SEQ ID NO: 8, SEQ ID NO: 9, SEQ ID NO: 10, SEQ ID NO: 11 and SEQ ID NO: 12.

13. The isolated nucleic acid molecule of claim 12, wherein said protein is the protein part of a human interleukin-9 receptor glycoprotein or a murine interleukin-9 receptor glycoprotein.

14. An expression vector comprising the isolated nucleic acid molecule of claim 12, wherein said nucleic acid molecule is operably linked to promoter.

15. The vector of claim 14, further comprising a marker sequence.

16. The vector of claim 15, wherein said marker sequence is a resistance marker.

17. The vector of claim 14, wherein said vector is a plasmid.

18. A microorganism transformed with the expression vector of claim 14.

19. The microorganism of claim 18 wherein said microorganism is *Escherichia coli*.

20. A cell line transfected with the expression vector of claim 14.

21. The cell line of claim 20 wherein said expression vector is a baculovirus vector.

22. The cell line of claim 20, wherein said cell line is a eukaryotic cell line.

23. The cell line of claim 21, wherein said cell line is a CHO cell or a COS cell.

* * * * *